US010235749B2

(12) United States Patent
Magana (10) Patent No.: US 10,235,749 B2
(45) Date of Patent: Mar. 19, 2019

(54) FOOD PROCESSING METHOD AND SYSTEM

(71) Applicant: Hill's Pet Nutrition, Inc., Topeka, KS (US)

(72) Inventor: Moses Alexander Magana, Topeka, KS (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/540,050

(22) PCT Filed: Dec. 27, 2014

(86) PCT No.: PCT/US2014/072456
§ 371 (c)(1),
(2) Date: Jun. 27, 2017

(87) PCT Pub. No.: WO2016/105441
PCT Pub. Date: Jun. 30, 2016

(65) Prior Publication Data
US 2017/0352150 A1 Dec. 7, 2017

(51) Int. Cl.
*G06T 7/00* (2017.01)
*B65B 57/14* (2006.01)
(Continued)

(52) U.S. Cl.
CPC ............ *G06T 7/0008* (2013.01); *A23L 3/001* (2013.01); *A23L 3/003* (2013.01); *B65B 3/04* (2013.01);
(Continued)

(58) Field of Classification Search
CPC ... G06T 7/0002; G06T 7/0004; G06T 7/0006; G06T 7/0008; G06T 7/001; G06T 7/13;
(Continued)

(56) References Cited

U.S. PATENT DOCUMENTS 3,598,907 A * 8/1971 Drinkuth .............. G01B 11/022
348/127
3,769,028 A * 10/1973 Katz ........................ A23L 3/10
426/232
(Continued)

FOREIGN PATENT DOCUMENTS

EP 0375157 6/1990
EP 1630550 3/2006
(Continued)

OTHER PUBLICATIONS

International Search Report and Written Opinion of the International Searching Authority in International Application No. PCT/US2014/072456, dated Jul. 20, 2015.
(Continued)

*Primary Examiner* — Alexander Valvis
*Assistant Examiner* — Eduardo R Ferrero (57) ABSTRACT

A method and system for forming a packaged product (100) and ensuring that the packaged product (100) is adequately filled. In one aspect, the method includes forming a product (101); introducing the product (101) into a package (103), thereby forming a packaged product (100); obtaining an x-ray image (201) of the packaged product (100); analyzing the x-ray image (201) utilizing a processor (118) to identify whether bounded contours (200) exist in the x-ray image (201) for each of the bounded contours (200), the processor (118) determining whether the bounded contour (200) is a threshold defect based at least in part on bounded area (208) of the bounded contour (200) for each of the threshold defects, the processor (118) classifying the threshold defect as one of a plurality of pre-determined defect types; and determining a source of at least one of the threshold defects in the packaged product (100) based at least in part on the classification of the at least one of the threshold defects.

17 Claims, 4 Drawing Sheets

(51) Int. Cl.
| | |
|---|---|
| *B65B 3/04* | (2006.01) |
| *A23L 3/00* | (2006.01) |
| *G06T 7/13* | (2017.01) |
| *B65B 7/00* | (2006.01) |
| *B65B 25/22* | (2006.01) |
| *G06K 9/62* | (2006.01) |
| *B07C 5/34* | (2006.01) |
| *G01N 21/90* | (2006.01) |
| *B67C 3/00* | (2006.01) |

(52) U.S. Cl.
CPC ............... *B65B 7/00* (2013.01); *B65B 25/22* (2013.01); *B65B 57/145* (2013.01); *G06K 9/6267* (2013.01); *G06T 7/0004* (2013.01); *G06T 7/13* (2017.01); *A23V 2002/00* (2013.01); *B07C 5/3404* (2013.01); *B67C 3/007* (2013.01); *G01N 21/90* (2013.01); *G06T 2207/10116* (2013.01); *G06T 2207/30128* (2013.01)

(58) Field of Classification Search
CPC ......... G06T 7/136; G06T 2207/101116; G06T 2207/30128; G06T 2207/30108; G06K 9/6267; A23L 3/001; A23L 3/003; B65B 57/145; B65B 57/00; B65B 57/02; B65B 7/00; B65B 25/22; B65B 3/04; A23V 2002/00; B07C 5/3404; G01N 21/90; G01N 21/88; G01N 23/083; G01N 23/043; B67C 3/007; B67C 3/007
USPC ...................... 53/167, 52, 53, 54; 378/51–86
See application file for complete search history.

(56) References Cited

U.S. PATENT DOCUMENTS

| | | | | |
|---|---|---|---|---|
| 3,805,486 | A * | 4/1974 | Mahaffy | B65B 9/04 425/388 |
| 3,917,947 | A * | 11/1975 | Fenton | B07C 5/3416 209/524 |
| 3,958,078 | A | 5/1976 | Fowler et al. | |
| 3,995,164 | A * | 11/1976 | Ramsay | G01N 23/10 378/156 |
| 4,136,930 | A * | 1/1979 | Gomm | G01N 21/8851 250/223 B |
| 4,208,126 | A * | 6/1980 | Cheo | G01N 21/88 250/341.1 |
| 4,363,966 | A * | 12/1982 | Cheo | G01N 21/88 250/338.1 |
| 4,388,795 | A * | 6/1983 | Stohlquist | B65B 43/59 141/150 |
| 4,830,865 | A * | 5/1989 | McFarlane | A23B 7/0053 165/87 |
| 4,879,734 | A * | 11/1989 | Schreckendgust | G11B 15/67565 378/57 |
| 5,056,124 | A * | 10/1991 | Kakimoto | B07C 5/346 378/53 |
| 5,097,494 | A * | 3/1992 | Pantelleria | G11B 15/67565 378/109 |
| 5,143,199 | A * | 9/1992 | Evans | A23L 3/001 198/418.1 |
| 5,414,778 | A * | 5/1995 | Schwartz | B67D 1/1247 250/223 B |
| 5,602,890 | A * | 2/1997 | Gray | B07C 5/3404 378/56 |
| 5,724,786 | A * | 3/1998 | Singh | B29C 65/08 53/249 |
| 5,864,600 | A | 1/1999 | Gray et al. | |
| 6,201,892 | B1 * | 3/2001 | Ludlow | G01N 21/8806 250/559.34 |
| 6,252,980 | B1 * | 6/2001 | Schwartz | B67D 1/1247 356/427 |
| 6,272,204 | B1 | 8/2001 | Amtower et al. | |
| 6,704,441 | B1 * | 3/2004 | Inagaki | G01N 21/952 209/545 |
| 6,922,459 | B2 * | 7/2005 | Pipino | G01N 23/04 378/57 |
| 7,239,740 | B1 | 7/2007 | Fujieda | |
| 7,400,709 | B2 | 7/2008 | Gusterson | |
| 7,636,449 | B2 * | 12/2009 | Mirtich | G06F 9/451 382/100 |
| 7,792,247 | B2 * | 9/2010 | Schmied | A61J 3/074 378/53 |
| 7,903,864 | B1 | 3/2011 | Lina et al. | |
| 8,305,570 | B2 * | 11/2012 | Piana | G01N 21/51 356/239.6 |
| 9,170,213 | B2 * | 10/2015 | Runft | A61J 3/074 |
| 2005/0252574 | A1 * | 11/2005 | Khan | B65B 3/003 141/198 |
| 2006/0056583 | A1 * | 3/2006 | Heuft | B07C 5/3408 378/57 |
| 2007/0107801 | A1 * | 5/2007 | Cochran | B65B 3/36 141/153 |
| 2007/0265743 | A1 * | 11/2007 | Kojitani | G06K 9/6268 701/32.9 |
| 2008/0001104 | A1 * | 1/2008 | Voigt | G01N 21/8851 250/559.46 |
| 2008/0061240 | A1 * | 3/2008 | Heuft | G01F 23/0076 250/343 |
| 2008/0138475 | A1 * | 6/2008 | Heuft | B07C 5/3408 426/232 |
| 2010/0002834 | A1 * | 1/2010 | Gudmundson | G01N 23/04 378/53 |
| 2010/0097451 | A1 * | 4/2010 | Bruce | A61M 5/16831 348/61 |
| 2012/0222387 | A1 * | 9/2012 | Forestelli | B67B 3/26 53/52 |
| 2012/0269937 | A1 * | 10/2012 | Newman | A23L 3/003 426/232 |
| 2013/0287264 | A1 * | 10/2013 | Chen | G07D 7/2016 382/112 |
| 2014/0147015 | A1 | 5/2014 | Bajema et al. | |
| 2014/0177932 | A1 | 6/2014 | Milne et al. | |
| 2014/0294238 | A1 * | 10/2014 | Kolb | G01N 21/9027 382/103 |
| 2016/0052764 | A1 * | 2/2016 | Fuhrer | B67C 3/007 348/143 |
| 2016/0055390 | A1 * | 2/2016 | Skatter | G06T 7/10 382/203 |
| 2016/0252646 | A1 * | 9/2016 | Sarraiocco | G01V 5/0016 382/103 |
| 2016/0258880 | A1 * | 9/2016 | Smorgon | G01N 21/8806 |
| 2017/0015540 | A1 * | 1/2017 | Zoni | B65C 3/26 |

FOREIGN PATENT DOCUMENTS

| | | |
|---|---|---|
| JP | S63-140949 A | 6/1988 |
| JP | H04-130254 A | 5/1992 |
| JP | 2004-354100 A | 12/2004 |
| JP | 2007-017457 A | 1/2007 |
| WO | WO 2014/087946 | 6/2014 |

OTHER PUBLICATIONS

Sapphire Inspection Systems, 2014, "G20 High Speed Xray Inspection System," Product Sheet, http://www.sapphire-inspecetion.com.

* cited by examiner

FOOD PROCESSING METHOD AND SYSTEM

BACKGROUND

Consumer perception of product quality greatly influences purchasing decisions. Quality control is therefore an important aspect of industrial manufacturing processes. The testing of high-volume consumer products such as foodstuffs poses particular challenges. Such products are generally produced using continuous manufacturing processes at high speed. For example, a pet food canning operation might produce 800 to 900 cans per minute.

One approach to quality control is to take samples from a batch of products and subject the samples to off-line testing, using statistical analysis to estimate the rate of occurrence of defects in the batch. Although this provides an estimate of product quality, the sampling process is destructive and it is not feasible to test each unit of product. Thus, methods reliant upon sampling do not completely eliminate the risk of unacceptable products entering the supply chain.

It is desirable to provide automated, continuous monitoring of product quality. Various techniques for achieving this have been proposed. An important example is the use of x-ray inspection. In this method, a system takes x-ray images of packaged products. Foreign bodies, such as metal, glass or bone, appear in the x-ray image as dark regions. These dark regions may be detected using image processing software and those containing foreign bodies may be removed automatically from the production line. The image processing generally involves analysis of pixel contrast. Calibration of the x-ray imaging system is therefore of critical importance in these existing methods.

There remains a need in the art for improved methods for detecting consumer-relevant defects in packaged products, including ensuring that packaged products are adequately filled.

BRIEF SUMMARY

Exemplary embodiments according to the present disclosure are directed to a method and system for forming a packaged product and ensuring that the packaged product is adequately filled. In one aspect, the method includes: (a) forming a product; (b) introducing the product into a package, thereby forming a packaged product; (c) obtaining an x-ray image of the packaged product utilizing an x-ray apparatus; (d) analyzing the x-ray image utilizing a processor to identify whether bounded contours exist in the x-ray image; (e) for each of the bounded contours identified in step (d), the processor determining whether the bounded contour is a threshold defect based at least in part on bounded area of the bounded contour; (f) for each of the threshold defects identified in step (e), the processor classifying the threshold defect as one of a plurality of pre-determined defect types; and (g) determining a source of at least one of the threshold defects in the packaged product based at least in part on the classification of the at least one of the threshold defects.

In another aspect, the invention can be a system for forming packaged products, the system including: a product formation subsystem configured to form a gel or paste product; a filling subsystem configured to dispense the product into packages to form packaged products; an x-ray apparatus configured to generate an x-ray image of each of the packaged products; a memory device configured to store a plurality of pre-determined defect types; and a processor operably coupled to the x-ray apparatus and the memory device, the processor configured to; (1) analyze the x-ray images to determine whether bounded contours exist in the x-ray images; (2) for each of the bounded contours, determine whether the bounded contour is a threshold defect based at least in part on the bounded area of the bounded contour; and (3) for each of the threshold defects, classify the threshold defect as one of a plurality of pre-determined defect types.

In another aspect, the invention can be a method for ensuring a packaged product is adequately filled, the method including: (a) generating an x-ray image of the packaged product; (b) detecting at least one bounded contour in the image; (c) for each bounded contour detected in step (b), (i) determining a bounded area and (ii) identifying whether the bounded contour is a threshold defect based the bounded area; (d) for each of the threshold defects identified in step (c), (i) calculating a severity score based on the bounded area and (ii) classifying the threshold defect as one of a plurality of pre-determined defect types; and (e) rejecting the packaged product based on the severity score and the classified defect type.

In another aspect, the invention can be a system for ensuring packaged products are adequately filled, the system including; an x-ray apparatus configured to generate an x-ray image of a packaged product in a processing system; a memory device configured to store a plurality of pre-determined defect types; a rejection mechanism configured to remove the packaged product from the processing system; a processor operably coupled to the x-ray apparatus, the memory device, and the rejection mechanism, the processor configured to: detect at least one bounded contour in the image; for each of the bounded contours, (i) determine a bounded area and (ii) identify whether the bounded contour is a threshold defect based the bounded area; for each of the identified threshold defects, (i) calculate a severity score based on the bounded area and (ii) classify the threshold defect as one of a plurality of pre-determined defect types; and send an instruction to the rejection mechanism to remove the packaged product from the processing system, the instruction based on the severity score and the classified defect type.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Figure 1:
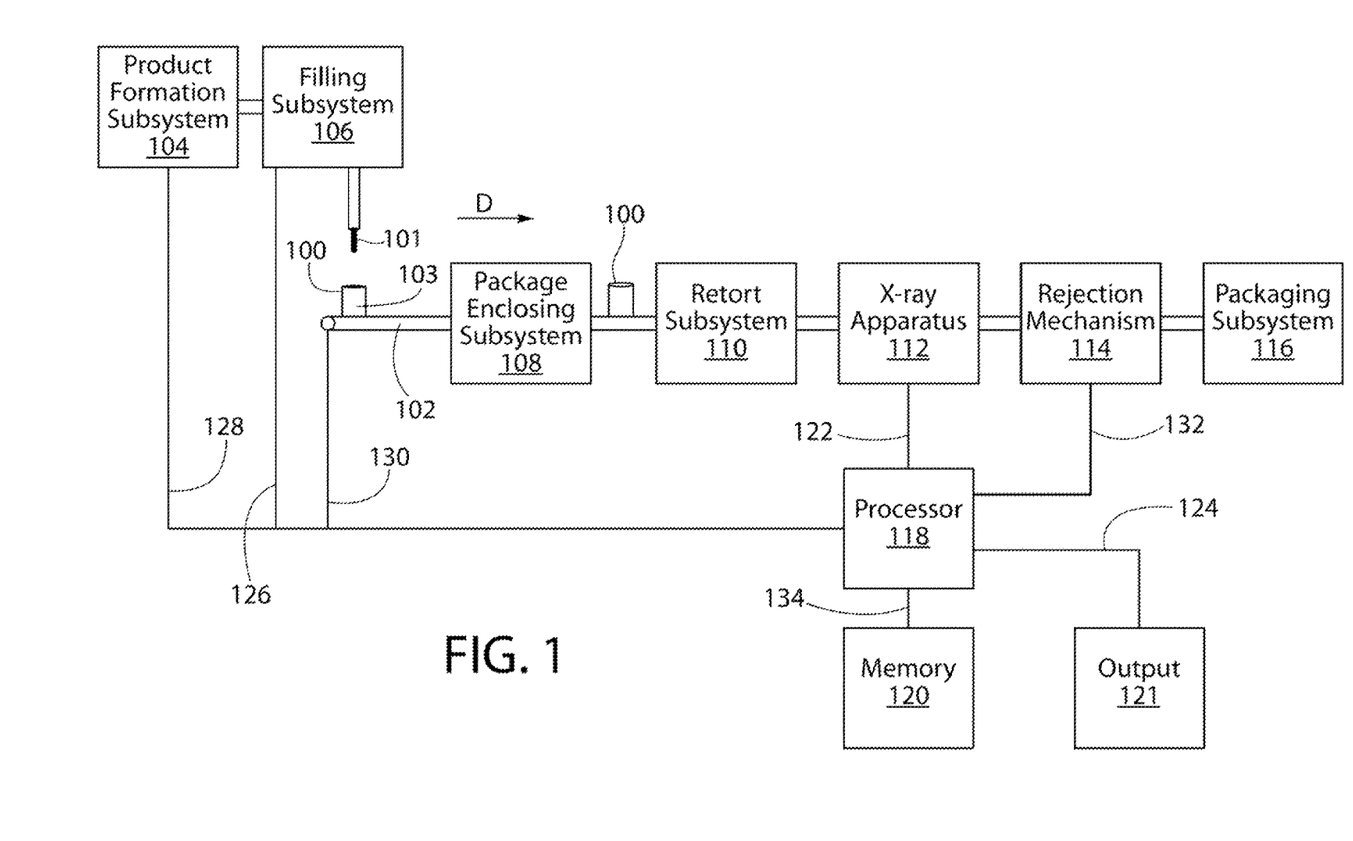
FIG. 1 is a block diagram of a system for forming packaged products in accordance with an embodiment of the present invention.

Referring now to FIG. 1, a system for forming packaged products 100 is shown. In the exemplified embodiment, the system inspects packaged products 100 and detects defects such as voids in the product 101. As will be discussed below, voids can be caused by a number of factors, including phase separation, the ingredients used, the rate of mixture, the resulting viscosity, and the flow rate at which the product 101 is dispensed in its package 103.

Products 101 formed from a paste or gel are inclined to develop voids. A paste is a suspension of a solid material in a fluid. Pastes can behave as solids or liquids depending on factors such as the mixture and the applied stress. These properties can cause phase separation during processing. The formation of gel generally involves the gelling of a liquid precursor in a container. In industrial manufacture, factors such as the flow rate at which the gel is dispensed and the movement of the packaged product 100 can lead to the formation of voids.

The system of FIG. 1 includes a product formation subsystem 104. In the exemplified embodiment, the product 101 formed is a loaf-type pet food. Such a pet food may comprise, by non-limiting example, a comminuted meat product suspended in a gelatinous matrix, e.g., a gelatinized starch. In other embodiments, the product formation subsystem 104 can form other products 101 capable of forming voids. The product 101 formed may be an oral care composition such as toothpaste or a tooth gel, or a human food product such as a potted meat product, or a personal care composition or cosmetic such as a cream.

In the exemplified embodiment, the product formation subsystem 104 includes an ingredient supply apparatus configured to supply a plurality of ingredients. The product formation subsystem 104 also includes a mixer configured to mix the supplied ingredients. The resulting product 101 of the product formation subsystem 104 has a viscosity.

In the exemplified embodiment, the formed product 101 is transferred from the product formation subsystem 104 to a filling subsystem 106. The fining subsystem 106 is configured to dispense the product 101 into packages 103 at a given flow rate and thereby form packaged products 100. The packaged products 100 can be transferred by a conveyor system 102 to a package enclosing subsystem 108 where the package 103 is enclosed with the product 101 therein.

In the exemplified embodiment, the conveyor system 102 is a conveyor belt configured to transport the packaged product 100 in direction D from the filling subsystem 106 to the package enclosing subsystem 108, from the package enclosing subsystem 108 to the retort subsystem 110, and from the retort subsystem 110 to the x-ray apparatus 112. In other embodiments, the conveyor system 102 can be any means of transferring the packaged product 100 from one location to another, including non-mechanical means.

The package 101 can be any container suitable for holding a product 101, including a can, tube, or pouch. In the exemplified embodiment, the package 103 is a metal can for containing pet food, and the enclosure of the package 103 forms an air-tight cavity. In other embodiments, the package 103 can be formed from a different material and/or be only partially enclosed.

In the exemplified embodiment, the packaged product 100 is next transferred to a retort subsystem 110. The retort subsystem 110 is configured to heat or cook the packaged product 100 to sterilize the product 101 and prevent microbial spoilage. In other embodiments, particularly in a system for forming non-food products 101, the retort subsystem 110 may be omitted.

After the retort subsystem 110, the packaged product 100 of the exemplified embodiment is transferred to an x-ray apparatus 112. X-ray imaging allows for the rapid, non-destructive inspection of packaged products 100. The x-ray apparatus 112 is configured to generate an x-ray image 201 of each of the packaged products 100. Such an image 201 can be generated by directing radiation towards the packaged product 100, and detecting at least a portion of the radiation directed toward the packaged product 100. X-ray imaging systems typically include an x-ray source and an x-ray detector. Generally, the x-ray source will be in the form of an x-ray tube. Other x-ray sources, such as a synchrotron light source, could be used. The x-ray detector may be, for example, a direct semiconductor detector or a scintillation counter. Other x-ray detectors include photographic plates and photostimulable phosphors.

Materials having different densities will absorb x-rays to a greater or lesser extent. This allows the presence of voids and defects to be identified using x-ray images 201. Voids will absorb x-rays to a lesser extent than the product 101, and will appear as bright regions in x-ray images 201. Further, different phases will have different densities and will be distinguishable from one another. Foreign bodies such as bones or metal fragments are also detectable, appearing as dark regions.

After generating an x-ray image 201 of the packaged product 100, the x-ray apparatus 112 of the exemplified embodiment transfers data associated with the x-ray image 201 to a processor 118 (via connection 122) configured to analyze the image 201. The processor 118 is operably coupled to the memory 120 (via connection 134). The processor 118 receives the data from the x-ray apparatus 112, as well as data stored in memory 120, to determine whether there is a defect and whether action must be taken. As will be described below, such actions may include rejecting a packaged product 100, adjusting the supply of ingredients at the product formation subsystem 104, and adjusting the flow rate at the filling subsystem 106. The processor 118 can also generate an output 121, which may comprise a display or report containing data related to the packaged products 100.

The processor 118 may be any type of properly programmed processing device, such as a computer or microprocessor, configured for executing computer program instructions (e.g. code). The processor 118 may be embodied in computer and/or server hardware of any suitable type (e.g. desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc. The processor 118 is configured with specific algorithms to enable it perform the functions discussed herein.

The memory 120 can be any device for storing data or programs, including a chip or disk. Further, the memory 120 need not form its own device, but can form part of other components, such as the processor 118.

Figure 2A:
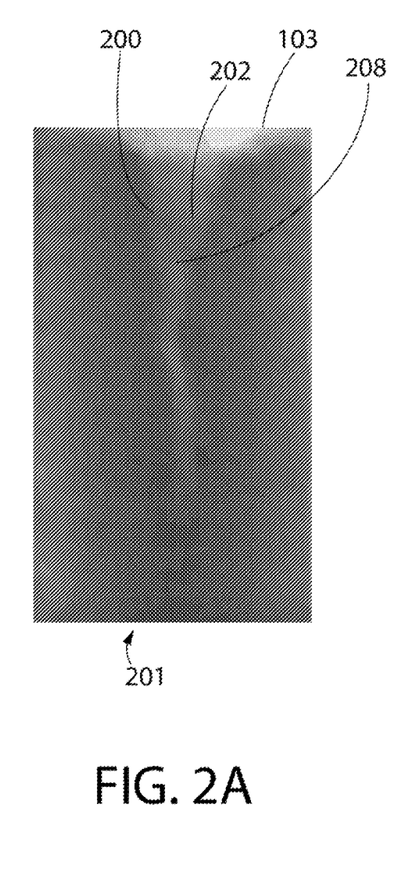
FIG. 2A is an x-ray image in which a spin hole is present in accordance with an embodiment of the present invention.
Figure 2B:
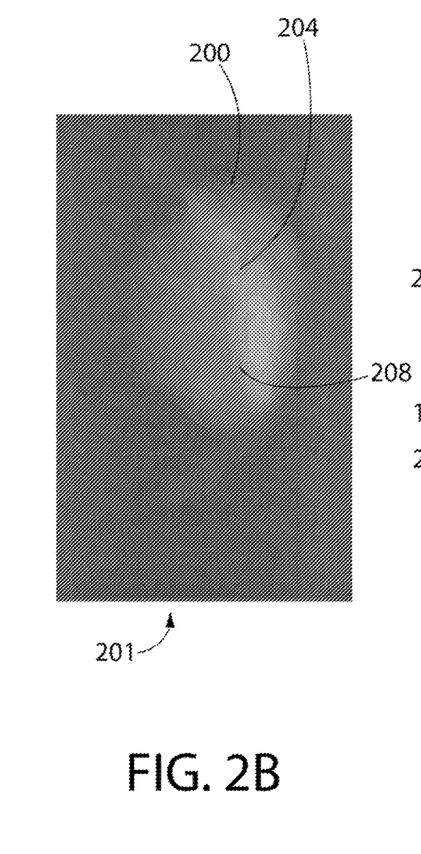
FIG. 2B is an x-ray image in which an air cell is present in accordance with an embodiment of the present invention.
Figure 2C:
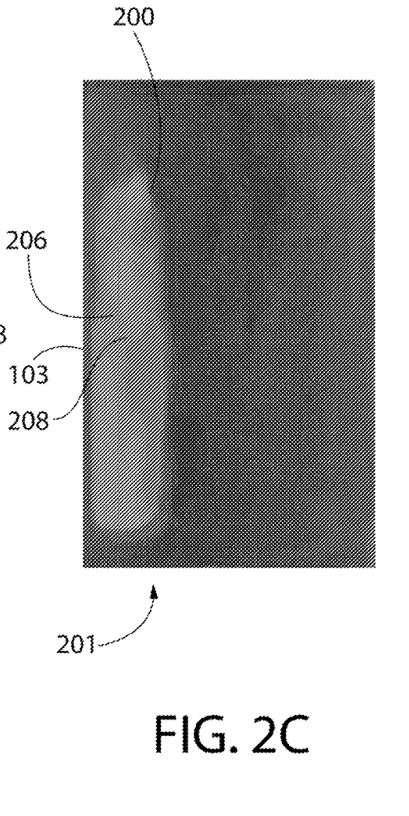
FIG. 2C is an x-ray image in which a side void is present in accordance with an embodiment of the present invention.

The process for identifying defects in x-ray images 201 and classifying such defects will now be described. Referring to FIG. 2, three x-ray images 201 taken by an x-ray apparatus 112 are shown, each having a different type of product defect. In the ideal case, the x-ray image 201 of the packaged product 100 would have an even color, indicating no variations in the density of the product 101. Low-density areas, corresponding to voids, however, appear as bright regions. It will be appreciated that the acceptability of void type defects to consumers is dependent upon factors such as the size, location, and shape of the defect.

FIG. 2A shows an x-ray image 201 in which a spin hole 202 is present. Such defects often have a tornado shape that extends from the top of the product package 103 downwardly. Such a defect can be caused by filling the package 103 too quickly as related to the product's viscosity. A spin hole 202 can often be prevented by adjusting the fill rate at the filling subsystem 100.

FIG. 2B shows an x-ray image 201 in which an air cell 204 is present. An air cell 204 is a bubble-like out and is generally found towards the center of the product package 103. An air cell 204 is typically caused by the product 101 viscosity being too thick. An air cell 204 can often be prevented by altering the product mixture at the product formation subsystem 104.

FIG. 2C shows an x-ray image 201 in which a side void 206 is present. A side void 206 is similar to an air cell 204, but is located at the side of the package 103. Like an air cell 204, a side void 206 is typically caused by the product 101 viscosity being too thick and can often be prevented by altering the mixture at the product formation subsystem 104.

It is to be understood that the foregoing defects are not the only types of defects that can occur in a packaged product 100. Voids at the bottom or corner of the package 103 are examples of other types of defects that could be identified.

In the exemplified embodiment, the processor 118 uses data from the x-ray images 201 to detect defects in the packaged product 100. The processor 118 can use pixel analysis to review the image 201. In the exemplified embodiment, the processor 118 further utilizes contour analysis of the x-ray images 201. By also using contour analysis, the manner in which the x-ray image 201 is collected is more flexible. Variations in the calibration of the imaging hardware, or even in the hardware itself, are readily tolerated.

The detection of defects by contour analysis is based on the assumption that the contours 10 present in the image 201 contain all of the information required to identify the defect. The system need not perform analysis on the points within the contours 10. This reduces the amount of data processed. The use of contour analysis with pixel analysis is therefore capable of being less computationally expensive than the use of pixel analysis alone. The combined use of contour analysis and pixel analysis can also utilize algorithms which are less complex than those generally used for pixel analysis alone. In alternative embodiments, the disclosed system can use contour analysis without pixel analysis.

A contour 10 is understood as a boundary between two regions, more specifically, the population of pixels that separate an object (the defect) from the background (the product 101). The contours 10 identified will be in the form of a mathematical description of the boundaries in the image 201. FIGS. 2A to 2C show contours 200 created by the respective defects 202, 204, 206. These defects form bounded contours 200 that will be discussed below.

Figure 3:
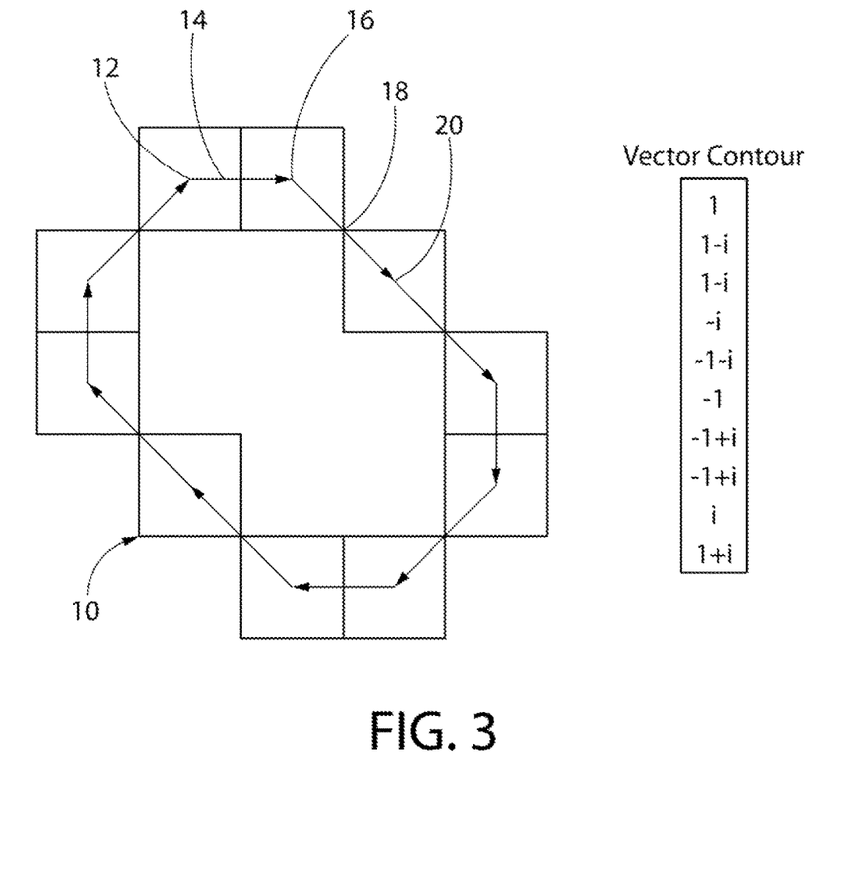
FIG. 3 is a diagram of a contour analysis in accordance with an embodiment of the present invention.

Referring now to FIG. 3, the contour analysis of the exemplified embodiment is discussed. The contour analysis uses as its input the pixels representing the contour 10. A starting point 12 is selected. An elementary vector of unit length 14 describing the offset between the starting point 12 and a second point 16 on the contour 10 is identified. A further elementary vector 18, describing the offset between the second point 16 and a third point 20 on the contour 10 is then generated, and so on. The contour 10 is scanned in this way until it has been fully described. Each vector is in the form of a complex number, a+ib, where "a" is the x-axis offset between two adjacent parts and "b" is the y-axis offset between the two points. A series of vectors describing the contour 10 of FIG. 3 is shown in the box at the right of the FIG.

Figure 4:
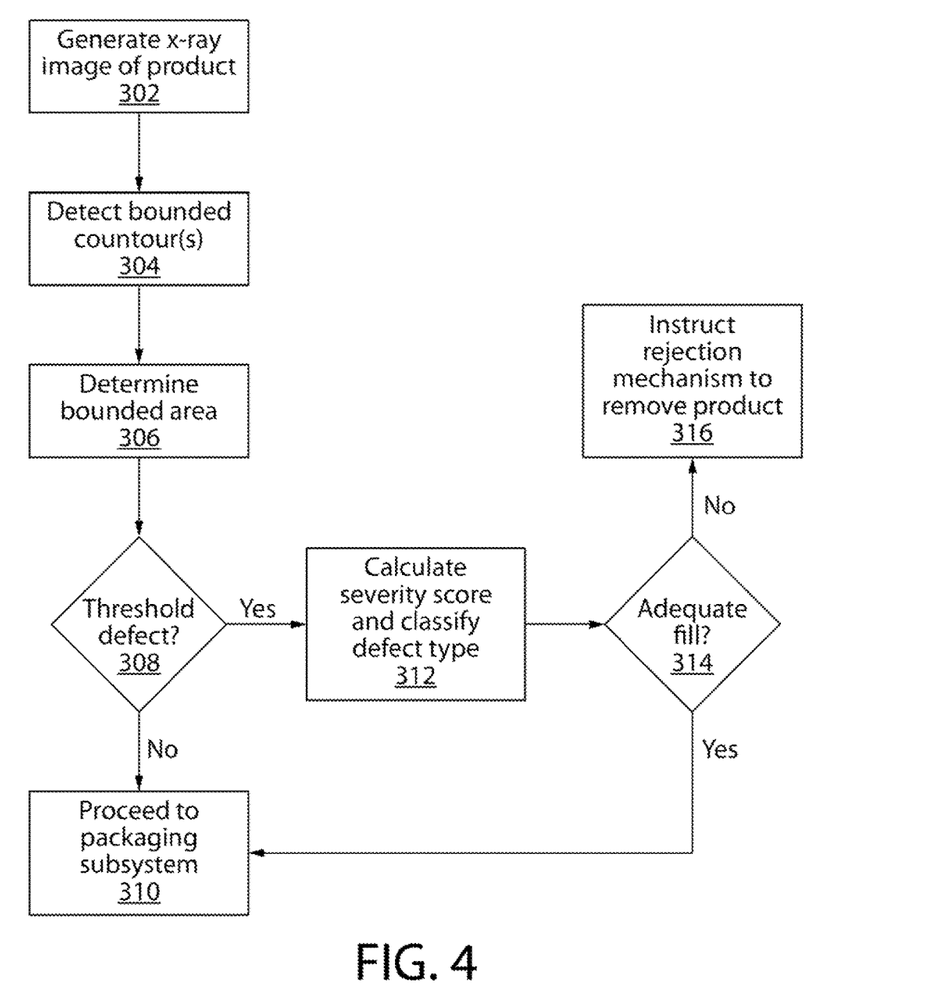
FIG. 4 is a now chart for a process for determining whether to reject a given packaged product in accordance with an embodiment of the present invention.

Referring now to FIG. 4, a process is shown for determining whether to reject a given packaged product 100. As discussed above, an x-ray image 201 is first generated by the x-ray apparatus 112 (step 302).

Next, using the aforementioned contour analysis, the exemplified process detects at least one bounded contour 200 in the image 201 (step 304). A bounded contour 200 is understood as a contour 10 that forms a boundary around a given region of the image 201. For example, in FIG. 2C, the contour 200 encircles a region at the center of the x-ray image 201 thereby bounding air cell 204. The area of the bounded contour 200 is referred to as the bounded area 208.

A bounded contour 200 can also be formed by both a contour 200 and the package 103 of the product 101, whereby the contour 200 and a portion of the package 103 collectively form a boundary around a region of the image 201. The defects in FIGS. 2A and 2C are examples in which the bounded contour 200 is formed in part by a contour 200 and in part by the package 103 of the product 101. Contours 10 which do not define (or with a package 103 define) a closed boundary are unlikely to correspond to defects and therefore can be excluded from further analysis.

The next step of the exemplified process is to determine the bounded area 208 for each bounded contour 200 (step 306). Standard programming techniques can be used to carry out this determination. In other embodiments, this step can be omitted.

Next, the process determines for each bounded contour 200 whether the bounded contour 200 is a threshold defect (step 308). In the exemplified embodiment, this determination of whether a bounded contour 200 is a threshold defect is based on the bounded area 208 of the bounded contour 200. Specifically, the determination is based on a ratio of the bounded area 208 to a total area of a packaged product portion 210 of the x-ray image 201. The packaged product portion 210 of the x-ray image 201 is understood as the portion of the x-ray image 201 attributable to the packaged product 100. For convenience, the x-ray images 201 of FIGS. 2A to 2C show only the packaged product portion 210.

By basing the determination of a threshold defect on the ratio of the bounded area 208 to a total area of a packaged product portion 210 of the x-ray image 201, the system can determine whether the threshold defect constitutes a significant portion of the overall packaged product 100. In other embodiments, the threshold defect determination can be based simply on an empirical value of the bounded area 208, or a factor unrelated to the area of the defect, such as location or shape. Reducing the number of contours 10 to be processed allows the method to be run more quickly. Small contours 10 will correspond to small defects and neglecting these defects may be appropriate depending, on the nature of the product 101 and consumer expectations. Additional filtering of the contours 10 may be carried out as desired.

In the exemplified embodiment, any contours 10 which are within regions bounded by a larger contour 200 may be excluded from the analysis. Generally, analysis of the internal features of defects does not yield useful information. Filtering the contours 10, 200 in this way reduces the number of calculations performed subsequently without impacting negatively on the results obtained.

If there is not a threshold defect, the product package 103 can proceed to the packaging subsystem 116 (step 310). But if a threshold defect is detected, for each threshold defect the process calculates the severity score and classifies the defect type based on the plurality of pre-determined defect types (step 312). In the exemplified embodiment, the severity score is based on the bounded area 208 of the bounded contour 200, specifically, the ratio of the bounded area 208 to a total area of a packaged product portion 210 of the x-ray image 201. In alternative embodiments, the severity score can be based on the bounded area 208 alone, or on another factor such as location or shape of the defect.

A plurality of pre-determined defect types is stored in memory 120. In the exemplified embodiment, the defect types include the aforementioned spin hole 202, air cell 204, and side void 206. For each threshold defect identified, the process classifies the threshold defect as one of the pre-determined defect types. The classification can be based on the location of the threshold defect in a packaged product portion 210 of the x-ray image 201. As discussed above, the spin hole 202 of FIG. 2A is located at the top of the packaged product portion 210, the air cell 204 of FIG. 2B is located toward the middle of the packaged product portion 210, and the side void 206 of FIG. 2C is located at the side of the packaged product portion 210. In other embodiments, the system can be configured to include pre-determined defect types corresponding with other locations in the packaged product portion 210, such as at the bottom or corner of the packaged product portion 210. Further, the classification of the defect type or a severity score could be based on data from multiple images of the packaged product 100, for example, images 201 of the packaged product 100 taken from different angles or locations.

In the exemplified embodiment, the classification of the threshold defect is also based on a shape of the threshold detect in a packaged product portion 210 of the x-ray image 201. As discussed above, the spin hole 202 of FIG. 2A takes a tornado shape, while the air cell 204 of FIG. 2B is a more circular bubble, and the side void 206 of FIG. 2C is a longer bubble. In other embodiments, the classification of the threshold defect can be based on location alone, shape alone, or any other factor or combination of factors discernible from the x-ray image 201.

Based on the calculations in step 312, the exemplified process then determines whether the product fill is adequate (step 314). If it is, the product package 103 can proceed to the packaging subsystem 116 (step 310). If it is not, the processor 118 instructs the rejection mechanism 114 to remove the packaged product 100 from processing (step 316). FIG. 1 shows the processor 118 in communication with the memory 120 (via connection 134) and the rejection mechanism 114 (via connection 132). If the data from the x-ray apparatus 112 (along with the data stored in memory 120) causes the processor 118 to conclude that the product package 103 is not adequately filled, the processor 118 sends instructions to the rejection mechanism 114 to remove the packaged product 100.

In the exemplified embodiment, the rejection of a packaged product 100 is based on the calculated severity score and the classified defect type. In other embodiments, the rejection can be based on alternative or additional factors. For example, the rejection can be further based on the sum total of the bounded areas 208 of the identified threshold defects, or a comparison of this sum total to the total area of a packaged product portion 210 of the x-ray image 201. Alternatively, the rejection could be based on multiple images 201 of the packaged product 100 taken from different angles or locations The rejection mechanism 114 of the exemplified embodiment is configured to mechanically remove packaged products 100 from the processing system to a bin upon rejection. In other embodiments, the rejection mechanism 114 can divert the packaged product 100 to any alternative destination, such as an inspection system or correction system. Further, this removal can be performed by any variety of means.

The above process can be repeated for a plurality of packaged products 100. Further, the system can be configured to discontinue the process based on the image analysis. In such an event, the processor 118 can send a signal to the conveyor system 102 (via connection 130 to discontinue the process until further action is taken.

The disclosed system and method can also be configured to determine the source of a threshold defect. In the exemplified embodiment, this determination is based on the classification of the threshold defect.

As discussed above, an air cell 204 or side void 206 is typically caused by the viscosity of the packaged product 100 being too thick. Such defects can often be prevented by altering the mixture at the product formation subsystem 104. In the exemplified embodiment, the system determines that the viscosity of the product 101 is the source of the least one of the threshold defects in the packaged product 100 based on the at least one of the threshold defects being classified as an air cell 204 or a side void 206 that is formed during a retort process. Further, the process can include adjusting the supply of one or more of the plurality of ingredients to adjust the viscosity of the product 101 being formed in the mixer to minimize and/or eliminate the formation of air cell 204 or side void 206 in a subsequent packaged product 100. Such adjustments can be carried out by adjusting valves or pumps or other mechanisms at the product formation subsystem 104.

As also discussed above, a spin hole 202 can be caused by filling the package 103 too quickly, and can often be prevented by adjusting the flow rate at the filling subsystem 106. In the exemplified embodiment, the system determines that the flow rate at the filling subsystem 106 is the source of the least one of the threshold defects in the packaged product 100 based on the at least one of the threshold defects being classified as a spin hole 202. Further, the process can include adjusting the flow rate at the filling subsystem 106 to prevent future defects to minimize and/or eliminate the formation of threshold defects in a subsequent packaged product 100. The flow rate can be altered by adjusting valves or pumps or similar mechanisms at the filling subsystem 106.

The determination of the source can be made by the processor 118 and the adjustment can be performed automatically by the processor 118 sending an instruction to the product formation subsystem 104 via connection 128 or to the filling subsystem 106 via connection 126. In other embodiments, a human operator can determine that the source of the threshold defects based on the classification of the threshold defects. Further, a human operator can carry out the adjustment at the product formation subsystem 104 or filling subsystem 106.

The processor 118 can be further configured to generate an output 121 for a packaged product 100 or a plurality of packaged products 100, the output 121 being transmitted via connection 124. In the exemplified embodiment, the output 121 comprises data including, for each threshold defect, the classified defect type and a severity score. The output 121 can include additional data, such as a suspected source of the defect, the time of the x-ray image 201, and an identifier for the packaged product 100. This output data can be utilized in a variety of ways. The data can be displayed on an electronic display adjacent the processing system for operators to review. The data can alternatively be used as a basis for a printed report. The data can be shown in raw format (with minimal processing), or it can be analyzed and shown in alternative formats, such as tables or charts summarizing results, or even alerts notifying an operator of a particular issue.

The system may be configured to store data relating to the images 201 processed to the memory 120. The saved data may include the severity score and classified defect type for each image 201 processed. The system may further provide statistical analysis of the saved data, for example identifying the frequency of occurrence of each type of defect. Such data are useful for identifying production problems, and for tracking the effects of changes to production processes.

The aforementioned processes may be provided as a computer program or stored as a computer readable medium including computer executable instructions for performing the method. The nature of the computer readable medium is not particularly limited. The medium may be magnetic, optical, magneto optical, flash storage, network-accessed storage or the like. Other media may be used.

Various modifications to the exemplified embodiments may be made. The aforementioned connections between the components of the system can take various forms, including wired and wireless connections. Further, two or more of the components may be formed integrally with one another. For example, the processor 118 and memory 120 may be formed integrally with the x-ray, apparatus 112. Further, components such as the rejection mechanism 114 are optional. Variants of rejection mechanism 114 may be used. For example, the rejection mechanism 114 may be replaced by a sorting mechanism for sorting packaged products 100 based on instructions from the processor 118.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications ma be made without departing from the scope of the present invention. Thus, the spirit and scope of the invention should be construed broadly as set forth in the appended claims.

What is claimed is:

1. A method for forming a packaged product and ensuring that the packaged product is adequately filled, the method comprising:
   a) forming a product, wherein forming the product comprises:
      a-1) supplying a plurality of ingredients to a mixer; and
      a-2) mixing the plurality of ingredients to form the product, the product having a viscosity;
   b) introducing the product into a package, thereby forming the packaged product;
   c) obtaining an x-ray image of the packaged product utilizing an x-ray apparatus;
   d) analyzing the x-ray image utilizing a processor to identify whether bounded contours exist in the x-ray image;
   e) for each of the bounded contours identified in step d), the processor determining whether the bounded contour is a threshold defect based at least in part on a bounded area of the bounded contour;
   f) for each of the threshold defects identified in step e), the processor classifying the threshold defect as one of a plurality of pre-determined defect types; and
   g) determining a source of at least one of the threshold defects in the packaged product based at least in part on the classification of the at least one of the threshold defects; and
   h) adjusting the supply of one or more of the plurality of ingredients to adjust the viscosity of the product being formed in the mixer to minimize and/or eliminate the formation of threshold defects in a subsequent packaged product,
   wherein the plurality of pre-determined defect types includes a spin hole, an air cell and a side void.

2. The method according to claim 1 wherein in step f) the processor classifies the threshold defect as one of the plurality of pre-determined defect types based at least in part on a location of the threshold defect in a packaged product portion of the x-ray image, and the identification of the threshold defect in step e) is based on an empirical value of the bounded area or a ratio of the bounded area to a total area of a packaged product portion of the x-ray image.

3. The method of claim 1,
wherein step g) comprises determining that the viscosity of the product is the source of the least one of the threshold defects in the packaged product based on the at least one of the threshold defects being classified as an air cell or a side void that is formed during a retort process; and
wherein step g) is performed by the processor, and
wherein step h) is performed automatically by the processor sending instructions to a product formation subsystem that includes the mixer and an ingredient supply apparatus.

4. The method according to claim 1, wherein:
step b) comprises dispensing the product into the package at a flow rate:
step g) comprises determining that the flow rate of the product in step b) is the source of the least one of the threshold detects in the packaged product based on the at least one of the threshold defects being classified as a spin hole; and the method further comprises
i) adjusting the flow rate of the product being dispensed in step b).

5. The method according to claim 1, wherein step f) comprises:
f-1) the processor classifying the threshold defect as one of the plurality of pre-determined defect types; and
f-2) the processor generating an output for the packaged product comprising data including the classified defect type of each threshold defect classified in step f-1) for the packaged product and a severity score for each threshold defect classified in step f-1), the severity score based at least in part on the bounded area of the contour.

6. The method according to claim 5 further comprising: rejecting the packaged product based on at least one of (i) the severity score of at least one of the threshold defects and (ii) the classified defect type of the at least one threshold defect.

7. The method according to claim 1, wherein the bounded contours of the x-ray image are formed partially by the product and partially by the package.

8. A system for forming packaged products, the system comprising:
a product formation subsystem configured to form a gel or paste product;
a filling subsystem configured to dispense the product into packages to form packaged products;
an x-ray apparatus configured to generate an x-ray image of each of the packaged products;
a memory device configured to store a plurality of pre-determined defect types; and
a processor operably coupled to the x-ray apparatus and the memory device, the processor configured to: (1) analyze the x-ray images to determine whether bounded contours exist in the x-ray images; (2) for each of the bounded contours, determine whether the bounded contour is a threshold defect based at least in part on the bounded area of the bounded contour; and (3) for each of the threshold defects, classify the threshold defect as one of a plurality of pre-determined detect types,
wherein the plurality of pre-determined defect types includes a spin hole, an air cell, and a side void; and
wherein the classification of the threshold defect as one of the plurality of pre-determined defect types is based on a shape of the threshold defect in a packaged product portion of the x-ray image.

9. The system according to claim 8 further comprising:
a package enclosing subsystem configured to enclose the packages having the product therein;
a retort subsystem configured to cook the packaged product; and, a conveyor system for transporting the packaged product from the filling subsystem to the package enclosing subsystem, from the package enclosing subsystem to the retort subsystem, and from the retort subsystem to the x-ray apparatus.

10. The system according to claim 9, wherein: the processor is further configured to determine a source of at least one of the threshold defects in the packaged product based at least in part on the classification of the at least one of the threshold defects, and wherein the classification of the threshold defect as one of the plurality of pre-determined defect types is based on a location of the threshold defect in a packaged product portion of the x-ray image.

11. A method for ensuring a packaged product is adequately filled, the method comprising:
a) generating an x-ray image of the packaged product;
b) detecting at least one bounded contour in the image;
c) for each bounded contour detected in step b), (i) determining a bounded area and (ii) identifying whether the bounded contour is a threshold defect based at least in part on the bounded area;
d) for each of the threshold defects identified in step c), (i) calculating a severity score based on the bounded area and (ii) classifying the threshold defect as one of a plurality of pre-determined defect types, wherein the plurality of pre-determined defect types includes a spin hole, an air cell, and a side void, and wherein the classification of the threshold defect as one of the plurality of pre-determined defect types is based on a shape of the threshold defect in a packaged product portion of the x-ray image; and
e) rejecting the packaged product based on the severity score and the classified defect type.

12. The method according to claim 11, wherein:
the classification of the threshold defect as one of the plurality of pre-determined defect types in step d) is based at least in part on a location or a shape of the threshold defect in a packaged product portion of the x-ray image, and the identification of the threshold defect in step c) is based on an empirical value of the bounded area or a ratio of the bounded area to a total area of a packaged product portion of the x-ray image.

13. The method according to claim 11, further comprising:
f) repeating steps a) to d) for a plurality of packaged products;
g) discontinuing the repeating of steps a) to d), the discontinuation based on the calculated severity scores and the classified threshold defects,
wherein the rejection of the packaged product in step e) is further based on a sum total of the at least one bounded area determined in step c).

14. A system for ensuring packaged products are adequately filled, the system comprising:
an x-ray apparatus configured to generate an x-ray image of a packaged product in a processing system;
a memory device configured to store a plurality of pre-determined defect types, wherein the plurality of pre-determined defect types includes a spin hole, an air cell, and a side void;
a rejection mechanism configured to remove the packaged product from the processing system; and a processor operably coupled to the x-ray apparatus, the memory device, and the rejection mechanism, the processor configured to:

detect at least one bounded contour in the image;

for each of the bounded contours, (i) determine a bounded area and (ii) identify whether the bounded contour is a threshold defect based at least in part on the bounded area;

for each of the identified threshold defects, (i) calculate a severity score based on the bounded area and (ii) classify the threshold defect as one of a plurality of pre-determined defect types, wherein the classification of the threshold defect as one of the plurality of pre-determined defect types is based on a shape of the threshold defect in a packaged product portion of the x-ray image; and send an instruction to the rejection mechanism to remove the packaged product from the processing system, the sending of the instruction based on the severity score and the classified defect type.

15. The system according to claim 14, wherein the processor is further configured to determine a source of at least one of the threshold defects in the packaged product based at least in part on the classification of the at least one of the threshold defects.

16. The system according to claim 14, wherein the classification of the threshold defect as one of the plurality of pre-determined defect types is based at least in part on a location of the threshold defect in a packaged product portion of the x-ray image.

17. The system according to claim 14, wherein the identification of the threshold defect is based on an empirical value of the bounded area or a ratio of the bounded area to a total area of a packaged product portion of the x-ray image.

* * * * *